US006428829B1

(12) United States Patent
Benbadis et al.

(10) Patent No.: US 6,428,829 B1
(45) Date of Patent: *Aug. 6, 2002

(54) STREPTOCOCCUS THERMOPHILUS STRAIN, FERMENTATION PROCESS USING SUCH STRAIN AND PRODUCT OBTAINED

(75) Inventors: Laurent Benbadis, Antony; Elisabeth Oudot, Bievres; Jacques De Villeroche, Versailles, all of (FR)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/411,658

(22) Filed: Oct. 4, 1999

Related U.S. Application Data

(63) Continuation of application No. 08/809,781, filed as application No. PCT/FR95/01254 on Sep. 28, 1995, now Pat. No. 6,056,979.

(30) Foreign Application Priority Data

Sep. 30, 1994 (FR) .............................. 94 11722

(51) Int. Cl.[7] .............................. A23C 9/12; C12N 1/20
(52) U.S. Cl. ........................ 426/34; 426/42; 426/583; 435/253.4
(58) Field of Search ................... 435/253.4; 426/34, 426/43, 42, 61, 580, 583

(56) References Cited

U.S. PATENT DOCUMENTS

| 4,416,905 A | * | 11/1983 | Lundstedt et al. | ............ 426/34 |
| 4,929,546 A | * | 5/1990 | Mayra-Makinen | ........... 435/29 |
| 4,954,450 A | * | 9/1990 | Brothersen et al. | ...... 435/252.4 |
| 4,968,513 A | * | 11/1990 | Watanabe et al. | ............. 426/42 |
| 5,409,718 A | * | 4/1995 | Klaver et al. | ................. 426/42 |
| 5,695,796 A | * | 12/1997 | Yamamoto et al. | ........... 426/43 |
| 6,056,979 A | * | 5/2000 | Benbadis et al. | ............. 426/34 |

FOREIGN PATENT DOCUMENTS

DE          33 00 123 A1      7/1984

OTHER PUBLICATIONS

Le Lait, vol. 71, No. 4, Elsevier, p. 445–461, Zourari et al., Ccaracterisation de bacteries lactiques thermophiles isolees de yaourts artisanaux grecs. I. Souches de Streptococcus salivarius subsp thermophilus.
Database WPI, Section Ch, Week 8824, Derwent Publications Ltd., London, Class D16, An 88–166505 & SU, A, 1 351 973 (Dairy Ind. Res. Inst.), Nov. 15, 1987.

* cited by examiner

Primary Examiner—Curtis E. Sherrer
(74) Attorney, Agent, or Firm—Finnegan, Henderson, Farabow, Garrett & Dunner, L.L.P.

(57) ABSTRACT

The present invention encompasses a *Streptococcus thermophilus* strain that has been deposited at the Collection Nationale de Cultures de Microorganismes (CNCM) under No. I-it 1477 and mutants that share similar milk acidification characteristics. The invention also covers processes for using the novel strain to prepare fermented dairy products and fermented products produced by these processes. Strain No. I-1477 possesses unique milk acidification properties that distinguish it from other related bacterial strains. Most importantly, the claimed Streptococcus strain exhibits both a rapid rate of acidification, which reduces the risk of bacterial contamination and extremely low post-acidification activity following fermentation, which helps preserve the fermentation products.

19 Claims, No Drawings

STREPTOCOCCUS THERMOPHILUS STRAIN, FERMENTATION PROCESS USING SUCH STRAIN AND PRODUCT OBTAINED

This is a continuation of application Ser. No. 08/809,781 filed Mar. 28, 1997, now U.S. Pat. No. 6,056,979 which is a National Stage of International Appln. No. PCT/FR95/01254 as originally filed on Sep. 28, 1995, all of which are incorporated herein by reference.

The present invention relates to a *Streptococcus thermophilus* strain, to the use of this strain for the production of fermented dairy products and to the products obtained using this strain.

The choice of lactic acid bacteria for the production of fermented dairy products calls into play various criteria, especially the acidifying activity and the formation of flavor components which provide the organoleptic properties of the product and the production of thickening agents which play a role in the texture and the unctuousness.

The acidifying activity is characterized essentially by three parameters: the kinetic of acidification, the titratable acidity and the final fermentation pH which determines the organoleptic characteristics of the product and its preservation quality, and the postacidification which develops during preservation of the product.

A high rate of acidification makes it possible to reduce the period during which the milk-based product is sensitive to contaminants (pH>4.7) and thereby to reduce the risk of bacterial contamination:

An increase in the rate of acidification also enhances the economics of the process by increasing the productivity and the flexibility of the industrial material.

The post-acidification properties of the strains are particularly important for the preservation or the products. Indeed, fresh fermented products are preserved at temperatures of between about 4° C. and 8° C. for a period in general not exceeding 4 weeks; but if the metabolic activity of the bacteria is reduced by preservation at low temperature, it is not blocked and it brings about the production of lactic acid from lactose, which has as a consequence a reduction in pH and an increase in the acid taste which damages the organoleptic properties of the product.

In addition to the criteria retained for their contribution to the quality of the products, other elements more specifically linked to the process play a role in the choice of the strains, such as the fermentation temperature, the rate of acidification and the resistance to phages.

The resistance to phages, is a very important criterion in the choice of the strains for reducing the risk of phage incidents during production which may block for a longer or shorter period the entire production for decontamination.

No *S. thermophilus* is so far known which exhibits a high rate of acidification and a high degree of acidity combined with a very low or practically zero post-acidification activity.

Indeed, it is generally observed that cultures of *S. thermophilus* which have a reduced post-acidification activity often show a limited acidifying activity during the fermentation, which does not allow the desired degree of acidity to be achieved in the products. In addition, these strains often have a slow growth and they require high inoculation levels and a longer incubation period which are incompatible with the economics of an industrial process.

The subject of the present invention is an *S. thermophilus* strain which has a rapid acidification kinetic allowing a high degree of acidity to be achieved and which does not post-acidify fresh fermented products during preservation.

More particularly, the present invention relates to an *S. thermophilus* strain DN-001 116 deposited at the Collection Nationale de Cultures de Microorganismes (CNCM) under No. I-1477 and mutants thereof which have similar milk acidification characteristics.

Mutant strains having milk acidifying characteristics similar to the deposited strain is intended to designate strains which may be obtained especially by mutation and selection from the reference strain and/or by genetic transformation with the aid of vectors.

The acidifying characteristics are an end-of-incubation pH of 4.6 in less than 4 hours and a pH variation at 28 days of less than 0.2 pH unit, preferably less than 0.1 unit.

The mutant strains may be obtained from the reference strain, especially by mutation and selection according to their acidifying properties. The mutation techniques are known, as well as the tests which make it possible to control the acidifying properties (especially Spinnier H. E., Corrieu G. "Automatic method to quantify starter activity based on pH measurement" J. of Dairy Research, 56 (1989) 755–764); by Roissart H. and Luquet F. M. Edition Lorica ISBN: 2-9507477-0-1).

These strains are more particularly advantageous for the preparation of all types of fermented milk products.

Accordingly, the present invention relates to a process for the preparation of fermented dairy products in which a milk substrate is fermented with at least one *S. thermophilus* strain.

It is also possible to provide, in this process, for the use of a combination of one or more bacterial strains, especially with other lactic acid bacteria such as *Lactobacillus bulgaricus, lactobacillus aciddphilus, Lactobacillus casei* or Bifidobacterium.

Preferably, the milk substrate is natural or reconstituted milk, skimmed or otherwise, or milk-based media or media based on products of dairy origin.

This substrate may comprise items commonly used for the preparation of milk desserts, solid items such as fruits, chocolate chips or cereals for example, but also sweetened products or liquid chocolates. The strain according to the invention in fact has the advantage of being resistant to sugars, which makes it possible to ferment sweetened products containing especially sucrose.

The present invention also relates to the fermented milk products obtained using this process, especially fresh fermented cheese, and yoghurts for example.

The products obtained using this strain have a mild taste and their organoleptic properties are preserved during storage.

The culture of the strains according to the invention, pure or in combination with other strains, may also be used as probiotic for human consumption or animal feed and also as ferment to be used in the process according to the invention.

Other characteristics and advantages of the present invention will appear on reading the examples below.

EXAMPLE 1

Comparison of the Rate of Acidification and the Post acidification Activity of Different *S. thermophilus* Strains A reconstituted skimmed milk containing 12% dry matter and enriched with 0.1% yeast extract is sterilized for 15 min at 121° C. An active culture of *S. thermophilus* comprising $10^8$ cells per milliliter is used to inoculate this medium at 1% (v/v). The starter culture is obtained after about 4 hours of incubation at 44° C. This starter culture is used to inoculate (1% v/v) 1 liter of reconstituted skimmed milk containing 12% dry matter, enriched with 0.1% yeast extract and previously pasteurized at 95° C. for 30 min. The inocuated milk is stirred and then incubated at 44° C. When the acidity reaches a pa of 4.6, the preparation is cooled for 16 hours at 4° C. This fermented milk is subjected to a test of preservation at 8° C. for 28 days. The pH after 28 days of preservation is compared for the different strains. The results are presented in Table 1. The strain I-1477 corresponds to the strain DN-001 116. Only the milk fermented with the *S. thermophilus* strain DN-001 116 has a practically zero post-acidification after 28 days of preservation 80° C. The strain DN-001 116 shows a rapid rate of acdification; a pH of 4.6 is reached in less than 4 hours of incubation at 440° C.

TABLE 1

| | Strain code | Incubation time | End of incubation pH | pH at 28 days | Difference |
|---|---|---|---|---|---|
| 01 | DN-001 003 | 4 h 46 min | 4.60 | 4.31 | 0.29 |
| 02 | DN-001 004 | 7 h 21 min | 4.62 | 4.26 | 0.36 |
| 03 | DN-001 013 | 7 h 18 min | 4.65 | 4.25 | 0.40 |
| 04 | DN-001 015 | 6 h 16 min | 4.65 | 4.30 | 0.35 |
| 05 | DN-001 022 | 5 h 18 min | 4.60 | 4.15 | 0.45 |
| 06 | DN-001 023 | 3 h 55 min | 4.59 | 4.19 | 0.40 |
| 07 | DN-001 025 | 6 h 48 min | 4.64 | 4.41 | 0.23 |
| 08 | DN-001 031 | 5 h 43 min | 4.60 | 4.40 | 0.20 |
| 09 | DN-001 032 | 4 h 18 min | 4.61 | 4.51 | 0.10 |
| 10 | DN-001 047 | 3 h 42 min | 4.60 | 4.18 | 0.42 |
| 11 | DN-001 054 | 4 h 19 min | 4.60 | 4.16 | 0.44 |
| 12 | DN-001 064 | 5 h 30 min | 4.60 | 4.10 | 0.50 |
| 13 | DN-001 067 | 4 h 09 min | 4.60 | 4.10 | 0.50 |
| 14 | DN-001 094 | 3 h 54 min | 4.61 | 4.08 | 0.53 |
| 15 | DN-001 107 | 3 h 45 min | 4.62 | 4.52 | 0.10 |
| 16 | DN-001 111 | 3 h 33 min | 4.60 | 4.11 | 0.49 |
| 17 | DN-001 116 | 3 h 45 min | 4.61 | 4.58 | 0.03 |
| 18 | DN-001 138 | 4 h 15 min | 4.60 | 4.12 | 0.48 |
| 19 | DN-001 143 | 4 h 05 min | 4.59 | 4.18 | 0.41 |
| 20 | DN-001 145 | 3 h 40 min | 4.60 | 4.17 | 0.43 |
| 21 | DN-001 147 | 6 h 09 min | 4.64 | 4.11 | 0.53 |
| 22 | DN-001 156 | 4 h 24 min | 4.60 | 4.12 | 0.48 |
| 23 | DN-001 162 | 4 h 05 min | 4.60 | 4.14 | 0.46 |
| 24 | DN-001 171 | 5 h 30 min | 4.58 | 4.08 | 0.50 |
| 25 | DN-001 181 | 4 h 33 min | 4.61 | 4.11 | 0.50 |
| 26 | DN-001 223 | 5 h 30 min | 4.60 | 4.21 | 0.39 |
| 27 | DN-001 225 | 3 h 54 min | 4.60 | 4.25 | 0.35 |
| 28 | DN-001 228 | 4 h 35 min | 4.61 | 4.16 | 0.45 |
| 29 | DN-001 230 | 6 h 15 min | 4.64 | 4.20 | 0.44 |
| 30 | DN-001 236 | 5 h 30 min | 4.63 | 4.10 | 0.53 |
| 31 | DN-001 242 | 3 h 51 min | 4.61 | 4.11 | 0.50 |
| 32 | DN-001 276 | 5 h 25 min | 4.60 | 4.18 | 0.42 |
| 33 | DN-001 277 | 3 h 35 min | 4.61 | 4.20 | 0.41 |
| 34 | DN-001 280 | 6 h 00 min | 4.62 | 4.10 | 0.52 |
| 35 | DN-001 289 | 4 h 50 min | 4.61 | 4.06 | 0.55 |
| 36 | DN-001 342 | 5 h 30 min | 4.60 | 4.53 | 0.07 |
| 37 | DN-001 343 | 3 h 55 min | 4.62 | 4.25 | 0.37 |

EXAMPLE 2

Comparison of the Post-acidification Activity of the *S. thermophilus* Strain 001 116 with Other *S. thermophilus* Strains The starter culture is prepared as in Example 1. This starter culture is used to inoculate (1% v/v) 1 liter of reconstituted skimmed milk containing 12% dry matter, enriched with 0.1% yeast extract and previously pasteurized for 30 min at 95° C. The inoculated milk is stirred and then incubated at 40° C. When the acidity reaches 80° D., the preparation is cooled for 16 hours at 40° C. This fermented milk is subjected to a test of preservation at 80° C. for 28 days. Table 2 presents the incubation time and the variation of the pH and of the Dornic acidity during storage at 80° C. for 28 days.

TABLE 2

| Strain code | Incubation time | Dornic acidity and pH at end of incubation | Dornic acidity and pH at 24 h | Dornic acidity and pH at 28 days | Dornic acidity and pH difference for 28 days |
|---|---|---|---|---|---|
| 001 116 | 3 h 25 min | 80° D, 4.80 | 86° D, 4.77 | 92° D, 4.63 | +12° D, −0.17 |
| ST25 | 5 h 30 min | 80° D, 4.75 | 86° D, 4.77 | 95° D, 4.57 | +15° D, −0.20 |
| ST44 | 3 h 55 min | 80° D, 4.75 | 88° D, 4.71 | 111° D, 4.35 | +21° D, −0.40 |

The post-acidification by the strain ST25 is comparable to that of the strain DN-001 116 but its acidification rate is much slower. The strain ST44, which exhibits a satisfactory acidification rate, shows a very high post-acidification.

EXAMPLE 3

Stability of a Fermented Ultrafiltered Milk Prepared with the Strain DN 001 116

A mixture composed of an ultrafiltered milk retentate containing 6% protein (NT-NPN×6.38) and cream containing 40% fat is prepared. The proportion of eacn of the two constituents is 82% retentate and 18% cream. 0.03% (w/w) casein hydrolysate is added. The content of the mixture is 5.3% protein and 7.2% fat. The preparation is subjected to a preheating at 75° C., a homogenization at 75° C. and at 200 bar, and then to a pasteurization at 95° C. for 8 min before cooling to 40° C. The mixture is then inoculated with a frozen concentrated preparation of the strain DN-001 116 in an amount of 30 g/100 L of a starter culture at 9×10$^9$ CFU/g. The inoculated mixture is incubated at 40° C. until a pH of about 4.7 is obtained. After settling of the curd and after discharging the curd, it is made into a smooth paste in a suitable valve before cooling to 20° C. in a plate exchanger. The smoothed and cooled product is then packaged in 1 kg pots. These pots, after palletization, pass inside a cold-air tunnel so as to cool the product to 4° C. The product is then subjected to a test of preservation at 4° C. and at 10° C. The results are presented in Table 3.

TABLE 3

| | Preservation at 4° C. | | Preservation at 10° C. | |
|---|---|---|---|---|
| Number of days | pH | Tasting | pH | Tasting |
| 0 | 4.70 | (+++) | 4.70 | (+++) |
| 3 | 4.66 | (+++) | n.d. | (+++) |
| 12 | 4.66 | (+++) | 4.66 | (+++) |
| 24 | 4.63 | (++) | 4.58 | (++) |

(+++) good, very mild
(++) good, mild

These results confirm that the *S. thermophilus* strain DN-001 116 exhibits a very reduced post-acidification at 4° C. and at 10° C.

EXAMPLE 4

Phage-resistance Character of the *S. thermophilus* Strain DN-001 116

60 phages of *S. thermophilus* were isolated over 10 years of production and in factories in different geographical areas. Analysis of their host spectrum made it possible to classify them into 7 subgroups. The resistance of the strain DN-001 116 was tested for phages representative of these 7 subgroups (φ15, φ57, φ47, φ77, φ76, φ29, φ65), the titer of the phages exceeded $10^7$ Plaque Forming Units/ml (The phages underlined have been described in the publication Biochimie (1990) 72, 855–862). The strain DN-001 116 is resistant to all the phages tested.

EXAMPLE 5

Resistance to Sugars

The procedure is carried out as in Example 3, but by adding to a medium to be fermented varied quantities of sucrose; the time for the target pH to be obtained is measured:

| medium containing 9% sucrose: | pH 4.7 | 620 min |
| medium containing 13% sucrose: | pH 4.7 | 920 min |

The *Streptococcus thermophilus* strain has been deposited at the Collection Nationale de Cultures de Microorganismes (CNCM) under No. I-1477 on the date of Sep. 22, 1994

What is claimed is:

1. An isolated culture of mutant strain of the *S. thermophilus* strain *deposited at Collection Nationale de Cultures de Microorganismes* (CNCM) under No. I-1477, wherein said mutant strain has milk acidification characteristics comprising an acidification of milk products to a pH of 4.6 in less than 4 hours and a pH variation of less than 0.2 unit following storage of said milk products at 8° C. for 28 days.

2. The mutant strain according to claim 1, wherein the mutant strain is obtained by mutation and selection for its acidification characteristics.

3. A process for preparing fermented dairy products, wherein said process comprises fermenting a milk substrate with at least one *S. thermophilus* strain according to claim 1.

4. The process according to claim 3, wherein the fermentation is carried out in the presence of at least one other strain of bacterium.

5. The process according to claim 4, wherein the other strain of bacterium is a lactic acid bacterium.

6. The process according to claim 5, wherein the lactic acid bacterium is is selected from the group consisting of: *Lactobacillus bulgaricus, Lactobacillus acidophilus, Lactobacillus casei*, and Bifidobacterium.

7. The process according to claim 3, wherein the milk substrate is milk.

8. The process according to claim 3, wherein the substrate contains solid items.

9. The process according to claim 8, wherein the solid items comprise fruits, chocolate products, or cereals.

10. Fermented Products obtained using the process according to claim 3.

11. Fermented products obtained using the process according to claim 4.

12. Fermented products obtained using the process according to claim 5.

13. Fermented products obtained using the process according to claim 6.

14. Fermented products obtained using the process according to claim 7.

15. Fermented products obtained using the process according to claim 8.

16. Fermented products obtained using the process according to claim 9.

17. A process for preparing fermented dairy products, wherein said process consists of fermenting a milk substrate with a *S. thermophilus* strain according to claim 1.

18. The *Streptococcus thermcphilus* strain according to claim 1, wherein the strain is phage-resistant.

19. The *Streptococcus thermophilus* strain according to claim 1, wherein the pH variation is less than 0.1 unit following storage of said milk products at 8° C. for 28 days.

* * * * *

UNITED STATES PATENT AND TRADEMARK OFFICE
CERTIFICATE OF CORRECTION

PATENT NO.    : 6,428,829 B1
DATED         : August 6, 2002
INVENTOR(S)   : Laurent Benbadis, Elisabeth Oudot and Jacques DeVilleroche It is certified that error appears in the above-identified patent and that said Letters Patent is hereby corrected as shown below:

<u>Title page,</u>
Item [57], ABSTRACT,
Line 4, "No. I-it 1477" should read -- No. I-1477 --.

<u>Column 5,</u>
Lines 26-27, "deposited at Collection Nationale de Cultures *de* Microorganismes" should read -- deposited at Collection Nationale de Cultures de Microorganismes --.

<u>Column 6,</u>
Line 4, "is is selected" should read -- is selected --.
Line 14, "Products" should read -- products --.
Line 33, "*thermcphilus*" should read -- *thermophilus* --.

Signed and Sealed this

Twenty-eighth Day of January, 2003

JAMES E. ROGAN
*Director of the United States Patent and Trademark Office*